United States Patent [19]

Hell et al.

[11] Patent Number: 5,294,638
[45] Date of Patent: Mar. 15, 1994

[54] PHENYALKYLAMINOALKYL COMPOUNDS AND PHARMACEUTICAL COMPOSITIONS CONTAINING THEM

[75] Inventors: Insa Hell, Hannover; Ulf Preuschoff, Laatzen; Hermann Kraehling, Sehnde; Samuel David; Ivan Ban, both of Hannover, all of Fed. Rep. of Germany; Marie-Odile Christen, Suresnes Cedex, France

[73] Assignee: Kali-Chemie Pharma GmbH, Hannover, Fed. Rep. of Germany

[21] Appl. No.: 5,457

[22] Filed: Jan. 19, 1993

Related U.S. Application Data

[63] Continuation of Ser. No. 806,302, Dec. 13, 1991, abandoned.

[30] Foreign Application Priority Data

Dec. 19, 1990 [DE] Fed. Rep. of Germany ....... 4040632

[51] Int. Cl.⁵ .................. A61K 31/135; A61K 31/36; C07C 211/19; C07D 317/58
[52] U.S. Cl. ..................... 514/452; 514/466; 514/654; 514/655; 549/363; 549/440; 549/443; 564/367; 564/369; 564/374; 564/384; 564/389; 564/391
[58] Field of Search ............... 564/367, 369, 374, 384, 564/389, 391; 549/363, 440, 443; 514/452, 466, 654, 655

[56] References Cited

U.S. PATENT DOCUMENTS

| | | | |
|---|---|---|---|
| 3,472,845 | 10/1969 | Thiele | 260/247.7 |
| 3,703,554 | 11/1972 | Bordenca | 260/583 |
| 3,845,048 | 10/1974 | Baronnet | 260/247.7 |

FOREIGN PATENT DOCUMENTS 1260571 11/1956 France .
471075 5/1906 Switzerland .

*Primary Examiner*—Richard L. Raymond
*Attorney, Agent, or Firm*—Evenson, McKeown, Edwards & Lenahan

[57] ABSTRACT

Pharmacologically active compounds corresponding to the general formula I:

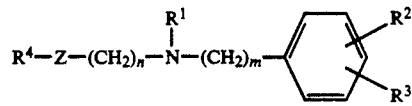

wherein
m represents 1–4,
n represents 2–5,
$R^1$ is hydrogen or lower alkyl,
$R^2$ is hydrogen, lower alkyl, lower alkoxy, halogen or trifluoromethyl, and
$R^3$ is hydrogen, lower alkyl, lower alkoxy or halogen, or
$R^2$ and $R^3$ are linked to adjacent carbon atoms and together form an alkylenedioxy group with 1–2 carbon atoms,
$R^4$ represents a saturated monocyclic or bicyclic hydrocarbon radical derived from terpenes and having 10 or 11 hydrocarbon atoms, and
Z represents oxygen, an N—$R^5$ group, wherein $R^5$ is lower alkyl, or if $R^4$ is a dihydronopyl radical, Z may also be sulfur,
and their acid addition salts.

16 Claims, No Drawings

PHENYLALKYLAMINOALKYL COMPOUNDS AND PHARMACEUTICAL COMPOSITIONS CONTAINING THEM

This application is a continuation of application Ser. No. 07/806,302, filed Dec. 13, 1991, now abandoned.

BACKGROUND OF THE INVENTION

The present invention relates to new dialkylamine derivatives which contain an alkyl radical substituted by an alkoxy, alkylthio or alkylamino group containing a monocyclic or bicyclic hydrocarbon radical, and an alkyl radical bearing an optionally substituted phenyl group. The invention also relates to a method for preparing these compounds and to pharmaceutical compositions containing them.

SUMMARY OF THE INVENTION

It is the object of the present invention to prepare new dialkylamino compounds having valuable pharmacological properties.

This and other objects of the invention are achieved by providing a compound corresponding to the formula I:

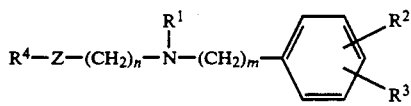

wherein
m represents 1-4,
n represents 2-5,
$R^1$ is hydrogen or lower alkyl,
$R^2$ is hydrogen, lower alkyl, lower alkoxy, halogen or trifluoromethyl, and
$R^3$ is hydrogen, lower alkyl, lower alkoxy or halogen, or
$R^2$ and $R^3$ are linked to adjacent carbon atoms and together form an alkylenedioxy group with 1-2 carbon atoms,
$R^4$ represents a saturated monocyclic or bicyclic terpene hydrocarbon radical with 10 carbon atoms, or a bicyclic hydrocarbon radical with 11 carbon atoms corresponding to the formula a:

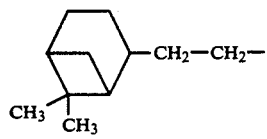

and
Z represents oxygen, an N—$R^5$ group in which $R^5$ is lower alkyl, or if $R^4$ is a group of formula a, Z also may be sulfur,
and psysiologically acceptable acid addition salts thereof.

Further objects of the invention are achieved by providing a pharmaceutical composition comprising a phenylalkylaminoalkyl compound according to the invention in an amount effective to exhibit a pharmacological activity selected from the group consisting of gastrointestinal mucosa protecting activity, gastrointestinal ulcer-inhibiting activity, and gastrointestinal spasmolytic activity, and at least one conventional pharmaceutical carrier or adjuvant, and by providing a method for preparing a phenylalkylaminoalkyl compound according to the invention.

DETAILED DESCRIPTION OF PREFERRED EMBODIMENTS

It has been discovered that the novel phenylalkylaminoalkyl compounds which contain monocyclic or bicyclic hydrocarbon radicals derived from terpenes and linked to the alkyl radical via oxygen, sulfur or an alkylamino group possess valuable pharmacological properties and in particular demonstrate a beneficial pharmacological action in the gastrointestinal tract. They are distinguished in particular by effects which protect the gastrointestinal mucosa and inhibit ulcers, while being readily tolerated and exhibiting low toxicity. In addition, they also have gastrointestinally effective spasmolytic properties.

The present invention therefore relates to novel phenylalkylaminoalkyl compounds of the general formula I:

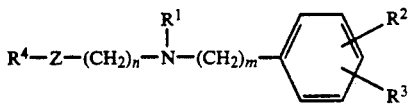

wherein
m represents 1-4,
n represents 2-5,
$R^1$ is hydrogen or lower alkyl,
$R^2$ is hydrogen, lower alkyl, lower alkoxy, halogen or trifluoromethyl, and
$R^3$ is hydrogen, lower alkyl, lower alkoxy or halogen, or
$R^2$ and $R^3$ are linked to adjacent carbon atoms and together form an alkylenedioxy group with 1-2 carbon atoms, and
$R^4$ represents a saturated monocyclic or bicyclic terpene hydrocarbon radical with 10 carbon atoms or a bicyclic hydrocarbon radical with 11 carbon atoms having the formula a:

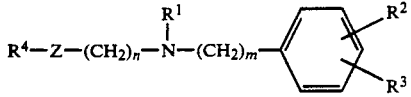

and
Z represents oxygen, an N—$R^5$ group, wherein $R^5$ is lower alkyl, or, if $R^4$ is a group of formula a, Z may also be sulfur,
and their physiologically acceptable acid addition salts.

In the compounds of formula I, $R^1$ may be hydrogen or preferably lower alkyl. A lower alkyl group $R^1$ may be straight-chain or branched and contain 1 to 4 carbon atoms, and represents in particular the methyl group.

If the substituents $R^2$ and/or $R^3$ of the phenyl group represent lower alkyl or alkoxy groups, these may be straight-chain or branched and contain 1 to 4, in particular 1 to 2, carbon atoms, and preferably represent methyl or methoxy. Fluorine, chlorine or bromine are particularly suitable as halogen substituents on the phenyl group.

The alkylene chain —$(CH_2)_m$— may contain 1 to 4, preferably 1 to 2, and particularly preferably 2, members. The alkylene chain —$(CH_2)_n$— may contain 2 to 5, preferably 2 or 3, members. Z preferably represents oxygen.

The hydrocarbon groups $R^4$ of the compounds of formula I are radicals having 10 or 11 carbon atoms derived from terpenes, and which may contain 17–19 hydrogen atoms. The radicals each contain several asymmetric centers, which may be in the R-configuration or S-configuration, so that the substances may exist in several diastereoisomeric forms. The claimed compounds of formula I according to the invention include the individual stereoisomeric forms of the compounds of formula I and mixtures thereof. Preferably the compounds of formula I contain hydrocarbon groups $R^4$ which can be derived from naturally occurring terpenes or can be prepared from naturally-occurring terpene derivatives. In nature, terpene derivatives, such as saturated terpene alcohols, occur in plants in more or less sterically pure form or as stereoisomer mixtures of variable composition. Accordingly, commercially available terpene derivatives which are generally prepared from natural products, may exist in a more or less sterically pure form or as stereoisomer mixtures. Within the scope of the present invention, particularly suitable compounds of formula I are those in which the hydrocarbon group $R^4$ is derived from natural and/or commercially available terpene derivatives.

In the preparation of compounds of formula I according to the invention, the configuration of the hydrocarbon radical $R^4$ of the starting compounds $R^4$—Z—H is retained, so that depending on the starting product used, stereoisomer mixtures or more or less stereoisomerically pure substances of formula I are obtained as end products of formula I.

Particularly suitable monocyclic or bicyclic hydrocarbon radicals with 10 or 11 carbon atoms include: 2-(6,6-dimethylbicyclo[3,1,1]hept-2-yl)-ethyl (=dihydronopyl) of formula a,

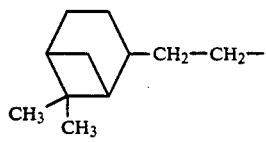

1-methyl-4-isopropylcyclohex-3-yl (=menthyl) of formula b,

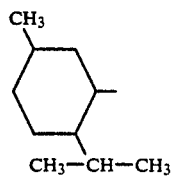

6,6-dimethylbicyclo[3,1,1]hept-2-ylmethyl (=myrtanyl) of formula c,

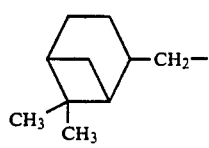

1,3,3-trimethylbicyclo[2,2,1]hept-2-yl (=fenchyl) of formula c,

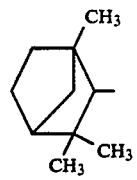

and 1,7,7-trimethylbicyclo[2,2,1]hept-2-yl (=bornyl) of formula e,

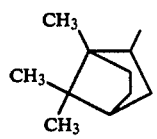

are particularly suitable as hydrocarbon radicals $R^4$. Of the aforementioned radicals $R^4$, the 2-(6,6-dimethylbicyclo[3,1,1]hept-2-yl)-ethyl radical of formula a (i.e. the dihydronopyl group) is particularly suitable. This radical contains asymmetric centers in positions 1, 2 and 5 of the bicycloheptane ring skeleton, each of which may be in the R-configuration or in the S-configuration. Within the scope of the present invention, the dihydronopyl compounds of formula I preferably contain a 2-(6,6-dimethylbicyclo[3,1,1]hept-2-yl)-ethyl group which is derived from a terpene alcohol which in turn is derived from natural (—)-β-pinene (=(1S,5S)-(—)-6,6-dimethyl-2-methylenebicyclo[3,1,1]heptane) in which the asymmetric centers in the 1- and 5-positions each have the S-configuration. Accordingly, the asymmetric centers in the 1- and 5-positions of the terpene ring skeleton in the 2-(6,6-dimethylbicyclo[3,1,1]hept-2-yl)-ethyl derivatives of formula I also have the S-configuration, whereas the asymmetric center in the 2-position may have either the S-configuration or the R-configuration, so that the corresponding compounds of formula I exist in two diastereomeric forms. Of these two dihydronopyl forms, the cis-form in which the asymmetric center in the 2-position of the bicycloheptane ring skeleton has an S-configuration, or mixtures which predominantly contain this form, are particularly preferred.

Furthermore, the 6,6-dimethylbicyclo[3,1,1]hept-2-yl-methyl radical of formula c (=myrtanyl radical) is highly suitable as the hydrocarbon group $R^4$. This radical contains asymmetric centers in positions 1, 2 and 5 of the bicycloheptane ring skeleton, each of which may be in the R-configuration or the S-configuration. Within the scope of the present invention, the myrtanyl compounds of formula I likewise preferably contain a 6,6-dimethylbicyclo[3,1,1]hept-2-yl-methyl group which is derived from natural (—)-β-pinene (=(1S,5S)-—-)-6,6-dimethyl-2-methylenebicyclo[3,1,1]heptane) in which the asymmetric centers in the 1- and 5-positions have an S-configuration. Accordingly, in the myrtanyl derivatives of formula I the asymmetric centers in the 1- and 5-positions of the bicycloheptane structure also are preferably in S-configuration, whereas the asymmetric center in the 2-position may have either the S-configuration or the R-configuration. Cis-myrtanyl derivatives in which all three asymmetric centers of the bicycloheptane ring skeleton have an S-configuration, or mixtures which predominantly contain this form, are particularly preferred.

Furthermore, the 1-methyl-4-isopropyl-cyclohex-3-yl radical of formula b (=menthyl radical) is suitable as the group $R^4$. This radical, which is derived from menthol, contains asymmetric centers in positions 1, 3 and 4 of the cyclohexyl structure, each of which may be in the R-configuration or in the S-configuration. In nature, the two enantiomeric forms 1R,3R,4S-1-methyl-4-isopropylcyclohexane-3-ol (=L-menthol) and 1S,3S,4R-1-methyl-4-isopropylcyclohexane-3-ol (=D-menthol) occur most frequently. Among the menthylsubstituted compounds of formula I, these two menthyl forms, particularly the L-menthyl form, or stereoisomer mixtures in which the L-menthyl form predominates, are preferred within the scope of the present invention as well.

The 1,3,3,-trimethylbicyclo[2,2,1]hept-2-yl radical of formula d (=fenchyl radical) and the 1,7,7-trimethylbicyclo[2,2,1]hept-2-yl radical of formula e (=bornyl radical) are also suitable as hydrocarbon groups $R^4$.

In the fenchyl radical $R^4$, asymmetric centers are contained in positions 1, 2 and 4 of the bicycloheptane ring skeleton, each of which may exist in the R-configuration or in the S-configuration. Within the scope of the present invention, fenchyl radicals derived from natural (+)-fenchol in which there is a 1S,4R-configuration are preferred, whereas the asymmetric center in the 2-position preferably has the R-configuration, but may also have the S-configuration.

The bornyl radical $R^4$ contains asymmetric centers in positions 1, 2 and 4 of the bicycloheptane ring skeleton, each of which may be in the R-configuration or the S-configuration. In natural bornyl derivatives the endobornyl radical occurs most frequently. The (−)-form (=1S,2R,4S-form) predominates over the (+)-form (=1R,2S,4R-form). Also within the scope of the present invention, bornyl derivatives containing a bornyl radical which is derived from natural borneol and which is present in the 1S,2R,4S-form, or mixtures which predominantly contain this form, are preferred.

The novel phenylalkylaminoalkyl compounds of formula I have valuable pharmacological properties, especially a beneficial pharmacological activity in the gastrointestinal tract. They are characterized by a protective action on the gastrointestinal mucosa and by a gastrointestinal ulcer-inhibiting effect, while being tolerated very well and exhibiting only low toxicity. It is known that non-steroidal anti-inflammatory drugs have a damaging effect on the mucosa barrier, and that gastrotoxic doses of such medicaments or other chemicals, such as alcohol, may lead to lesions and ulceration. This effect can be inhibited by the novel compounds according to the invention, which indicates a therapeutically protective action on the gastrointestinal mucosa. These effects can be demonstrated in standard pharmacological tests on animals.

DESCRIPTION OF THE PHARMACOLOGICAL TESTS

A. Determination of the inhibiting effect of the compounds against ethanol-induced lesions in rats.

Groups of 6 male rats each having a body weight of 160–180 g were used per test dose. The animals were kept without food for 24 hours, but had unlimited quantities of water available. The test substances were administered per os suspended in 0.5 ml of suspension medium per 100 g of animal weight. A control group of animals was given only the corresponding volume of the suspension medium. One hour after administration of the test substances, the animals were administered 0.5 ml 60%-strength ethanol per 100 g animal weight per os. The animals were sacrificed one hour after the administration of ethanol. The stomachs were removed, opened, and carefully rinsed. The number and size of the lesions formed in the mucosa were assessed. The evaluation took place in modified manner according to the method of O. Münchow (Arzneim. Forsch. (Drug Res.) 4, 341–344 (1954)). Average values and standard deviations were calculated, and the inhibiting effect of the test substances in % with respect to the control group was determined therefrom.

The following Table A gives results obtained according to the test method described above. The example numbers given for the compounds of formula I relate to the following preparative examples.

TABLE A

| Example No. | Dose p.o. (μmol/kg) | Inhibition of Ethanol-induced Lesions in Rat Stomachs (%) |
|---|---|---|
| 1 | 100 | 77 |
| 2 | 100 | 93 |
| 5 | 100 | 97 |
|  | 46 | 87 |
| 6 | 46 | 59 |
| 7 | 100 | 61 |
| 11 | 100 | 72 |
| 12 | 100 | 86 |
|  | 46 | 62 |
| 13 | 100 | 87 |
|  | 46 | 72 |
| 18 | 100 | 75 |
| 20 | 100 | 83 |
|  | 46 | 63 |
| 28 | 100 | 63 |

B. Determination of the minimum toxic dose.

Male mice each weighing 20–25 g were administered maximum doses of 300 mg/kg of the test substance per os. The animals were carefully observed for toxic symptoms for 3 hours. All symptoms and deaths over a period of 24 hours after administration were additionally recorded. If death or strong toxic symptoms were observed, additional mice were administered increasingly smaller doses until no more toxic symptoms occurred. The lowest dose which caused death or strong toxic symptoms is given as the minimum toxic dose in the following Table B.

TABLE B

| Example No. | Minimum Toxic Dose in Mice (mg/kg p.o.) |
|---|---|
| 1 | 100 |
| 5 | 300 |
| 6 | 300 |
| 7 | >300 |
| 11 | 300 |
| 12 | >300 |
| 13 | >300 |
| 18 | >300 |
| 20 | 300 |
| 28 | 300 |

In addition to a protective effect on the gastrointestinal mucosa and an ulcer-inhibiting activity, the compounds of formula I also have gastrointestinally active spasmolytic properties.

Due to their action in the gastrointestinal tract, the compounds of formula I are useful in gastroenterology as medicaments for larger mammals, in particular humans, for the prophylaxis and treatment of ulceration and/or damage to the gastrointestinal mucosa caused by gastrotoxic doses of medicaments or chemicals.

The doses to be used may differ from individual to individual, and will naturally vary depending on the type of condition to be treated, the substance used, and the manner of administration. For example, parenteral formulations will generally contain less active substance than oral preparations. Generally speaking, however, medicament forms containing 10 to 200 mg of active substance per individual dose are suitable for administration to larger mammals, in particular humans.

As medicaments, the compounds of formula I may be contained together with conventional pharmaceutical adjuvants in galenic preparations such as tablets, capsules, suppositories or solutions. These galenic preparations may be produced by known methods using conventional solid carriers, e.g. lactose, starch or talcum, or liquid paraffins, and using conventional pharmaceutical adjuvants such as tablet disintegrating agents, solubilizers or preservatives.

According to the invention, the novel compounds of formula I and their acid addition salts are obtained by
a) reacting compounds of the general formula II

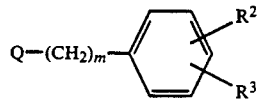

wherein
$R^2$, $R^3$ and m have the above meanings, and
Q represents the group

in which $R^1$ has the above meaning, or if m is other than 2, Q may represent a cleavable leaving group Y,
with compounds of the general formula III,

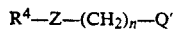

wherein
$R^4$, Z and n have the above meanings, and
Q' represents a cleavable leaving group Y, if Q is a group

or Q' represents a group

if Q is a cleavable leaving group Y, or
b) reducing compounds of the general formula IV

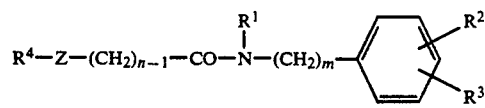

wherein $R^1$, $R^2$, $R^3$, $R^4$, Z, n and m have the above meanings, or
c) to prepare compounds of the general formula Ia,

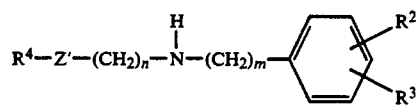

wherein $R^2$, $R^3$, $R^4$ and n have the above meaning, m' is 2-4 and Z' has the meaning given for Z with the exception of sulfur, from compounds of the general formula V,

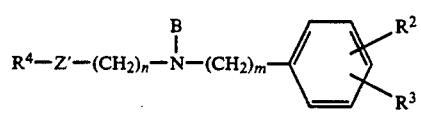

wherein $R^2$, $R^3$, $R^4$, Z', n and m' have the above meanings, and
B represents a hydrogenolytically cleavable group, by hydrogenolytically cleaving and eliminating the group B in a known manner, or
d) to prepare compounds of the general formula Ib,

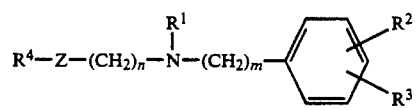

wherein $R^2$, $R^3$, $R^4$, Z, n and m have the above meanings, and $R^{1'}$ is lower alkyl, reacting compounds of the general formula VI

wherein $R^4$ has the above meaning and T represents the group ZH, wherein Z has the above meaning, or T represents a cleavable leaving group Y, in particular halogen, in known manner with compounds of the general formula VII

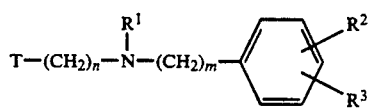

wherein $R^{1'}$, $R^2$, $R^3$, n and m have the above meanings, and T' represents a cleavable leaving group Y, in particular halogen, if T is the group ZH, or T' represents the radical ZH if T is a cleavable leaving group Y, and, if desired, alkylating resulting compounds of the general formula I wherein $R^1$ is hydrogen, to give corresponding compounds of formula I wherein $R^1$ is lower alkyl, and, if desired, converting free compounds of formula I into their acid addition salts, or converting the acid addition salts into the free compounds of formula I.

The reaction of compounds of formula II with compounds of formula III in accordance with method variant a) may take place in a known manner under standard conditions for the alkylation of amines. Preferably halogens, such as chlorine, bromine or iodine, or also organic sulfonic acid radicals, for example radicals of lower alkane sulfonic acids such as methanesulfonic acid, or of aromatic sulfonic acids such as benzene sulfonic acid or benzene sulfonic acids substituted by lower alkyl or halogen, e.g. toluene sulfonic acids or bromobenzene sulfonic acids, are suitable as leaving groups Y in the compounds of formula II or the compounds of formula III. The reaction is advantageously carried out in solution under basic conditions. Inert organic solvents, or alternatively an excess of the amine compound which is to be reacted, may serve as solvents. Examples of suitable inert organic solvents include lower alcohols, e.g. methanol, or dimethyl formamide, acetonitrile or alternatively ethers, in particular cyclic ethers such as tetrahydrofuran, or aromatic hydrocarbons such as benzene or toluene or mixtures of the aforementioned solvents. Advantageously, the reaction is carried out in the presence of at least one equivalent of an acid-binding base. Examples of suitable bases include inorganic bases such as alkali metal carbonates, or organic bases, in particular tertiary amines, for instance tertiary lower alkylamines such as triethylamine or N,N-dimethylaminopyridine, or optionally also an excess of the amine compound which is to be reacted.

The reaction temperature may vary depending on the of reagents used, and may be selected between 0° C. and boiling temperature of the solvent, in particular between about 20° C. and boiling temperature of the solvent. The reaction time may be between two and twelve hours depending on the reaction conditions selected. If $R^1$ is hydrogen, it is advantageous to use an excess of amine compound in order to avoid secondary reactions. The resulting compounds of formula I may readily be freed of any small impurities of by-products, e.g. by chromatographic purification.

The reduction of amides of formula IV to form compounds of formula I according to method variant b) may take place in a known manner using reducing agents suitable for reducing amides. In particular, complex metal hydrides such as lithium aluminium hydride, diborane, sodium borohydride in glacial acetic acid or diisobutyl aluminium hydride are suitable as reducing agents. The reduction takes place in a solvent which is inert under the reaction conditions, for example an ether, preferably a cyclic ether such as tetrahydrofuran, or a mixtures of a cyclic ether and an aromatic hydrocarbon such as toluene. The reaction temperature may be between room temperature and the boiling temperature of the solvent. The reaction time may be between 3 and 10 hours, depending on the reducing agent used and on the reaction conditions selected.

Compounds of formula Ia can be obtained from compounds of formula V according to method variant c) by means of catalytic hydrogenolysis in a known manner. Suitable hydrogenolytically cleavable groups B include, in particular, the benzyl radical or a benzyl radical which is substituted in its phenyl ring. The hydrogenolysis may be performed in the presence of catalysts suitable for hydrogenolytic debenzylation at a hydrogen pressure of 1 to 10 bar, in particular 1 to 6 bar, and at temperatures of 0 to 60° C. in a solvent which is inert under the reaction conditions. Examples of suitable catalysts include palladium on carbon, palladium hydroxide on carbon, and Raney nickel. Examples of suitable solvents include lower alcohols such as ethanol; ethyl acetate, acetic acid or aromatic hydrocarbons such as toluene or mixtures thereof, optionally also in admixture with water. Advantageously, the hydrogenolysis is carried out in an acidified medium, for instance in a reaction medium containing an addition of hydrochloric acid.

The reaction of compounds of formula VI with compounds of formula VII according to method variant d) may be carried out in a known manner according to conventional methods for forming ethers or thioethers or according to conventional methods for aminoalkylation, respectively.

Thus, for instance, compounds of the general formula VIc,

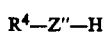

$$R^4-Z''-H$$

wherein $R^4$ has the above meaning and $Z''$ is oxygen or sulfur, are reacted with compounds of the general formula VIIa,

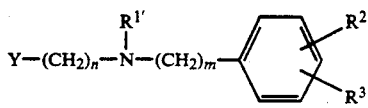

wherein $R^{1'}$, $R^2$, $R^3$, n, m and Y have the above meanings, in particular halides of formula VIIa, or compounds of the general formula VIb,

$$R^4-Y$$

wherein $R^4$ and Y have the above meanings, in particular halides of formula VIb, are reacted with compounds of the general formula VIIc,

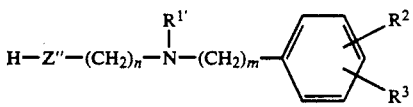

wherein $R^{1'}$, $R^2$, $R^3$, $Z''$, n and m have the above meanings. The reaction advantageously takes place in an organic solvent which is inert under the reaction conditions and in the presence of a strong base which is capable of reacting with the alcohols or thioalcohols of formulae VIc or VIIc to form the corresponding alcoholates or thioalcoholates. Examples of suitable strong bases include alkali metals, alkali metal hydrides, alkali metal amides or alkali metal hydroxides. Examples of suitable inert organic solvents include ethers, particularly cyclic ethers such as tetrahydrofuran or dioxane, or aromatic hydrocarbons such as benzene, toluene or xylene. If desired, the reaction may also be performed without the addition of a solvent. The reaction temperature may be between room temperature and boiling temperature of the reaction mixture, and the reaction time may be between 2 and 10 hours, depending on the reaction conditions.

If T or T' in the compounds of formula VI or the compounds of formula VII represents an $HMR^5$ radical, the reaction of the compounds may be carried out according to conventional methods for aminoalkylation. For instance, the reaction may be performed under the conditions given above for the reaction of compounds of formula II with compounds of formula III.

If desired, the resulting compounds of formula I in which $R^1$ is hydrogen may later be alkylated in a known manner to form the corresponding N-alkyl compounds. Suitable alkylation agents include alkyl halides, in particular iodides, alkyl sulfates or alkylsulfonic acid esters. Advantageously, the alkylation is carried out in an organic solvent which is inert under the reaction conditions, in the presence of a base such as an alkali metal carbonate or a tertiary organic amine, especially a tertiary lower alkylamine. Depending on the base used, dimethyl formamide, acetonitrile, cyclic ethers such as tetrahydrofuran or dioxane, aromatic hydrocarbons such as toluene, or alternatively lower alcohols are suitable as solvents. The reaction may take place at temperatures between room temperature and the boiling temperature of the solvent. The subsequent alkylation may also be carried out as a reductive alkylation in known manner by reacting with a lower aldehyde, in particular formaldehyde, under reducing conditions. For instance, the compounds may be reacted with the aldehyde in the presence of a reducing agent, for instance formic acid. If Z represents Z' and m represents m' in the compounds of formula I, the reductive alkylation may also take place by reacting the compound with the aldehyde and catalytically hydrogenating the reaction mixture. Palladium on carbon, for instance, is suitable as a hydrogenation catalyst.

The compounds of formula I may be isolated from the reaction mixture and purified in a known manner. Acid addition salts may be converted in conventional manner into the free bases, and if desired, these bases may be converted into pharmacologically acceptable acid addition salts in a known manner.

If desired, the individual stereoisomeric forms may be enriched and isolated from stereoisomer mixtures of the compounds of formula I by conventional separation methods, for instance fractional crystallization of suitable salts or chromatographic processes.

Examples of suitable pharmacologically acceptable acid addition salts of the compounds of formula I include salts thereof with inorganic acids, e.g. hydrohalic acids, in particular hydrochloric acid, sulfuric acid or phosphoric acid, or with organic acids, for instance lower aliphatic monocarboxylic or dicarboxylic acids such as maleic acid, fumaric acid, oxalic acid, lactic acid, tartaric acid or acetic acid, or sulfonic acids, for instance lower alkylsulfonic acids, such as methanesulfonic acid or benzene sulfonic acids optionally substituted in the benzene ring by halogen or lower alkyl, such as p-toluene sulfonic acid, or cyclohexylamine sulfonic acid.

The starting compounds of formula III may be obtained in known manner. Compounds of the general formula IIIa,

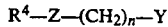
$R^4—Z—(CH_2)_n—Y$ wherein $R^4$, Z, n and Y have the above meanings, may for instance be obtained by converting the hydroxy group in compounds of the general formula X,

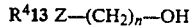
$R^4 13\ Z—(CH_2)_n—OH$ wherein $R^4$, Z and n have the above meanings, into a leaving group Y in a known manner. For instance, the compounds of formula X may be reacted in a known manner with thionyl chloride or with phosphorus halides in order to introduce a halogen radical Y. Sulfonic acid radicals Y may be introduced by acylating compounds of formula X in known manner with a corresponding sulfonic acid chloride.

Compounds of formula X may be prepared in a known manner starting from compounds of formula VIb. To prepare compounds of formula X in which Z is oxygen, compounds of formula VIb, in particular halides VIb, may be reacted, for instance, with a diol of the general formula XI,

$HO—(CH_2)_n—OH$ wherein n has the above meaning. An excess of the diol is advantageously used to avoid secondary reactions. The reaction may be performed under conventional conditions for forming an ether in the presence of a strong base such as an alkali metal or an alkali metal hydride, alkali metal amide or alkali metal hydroxide. To prepare compounds of formula X in which Z represents sulfur, alkali metal salts of compounds of the general formula VIe,

$R^4—SH$ wherein $R^4$ has the above meaning, which salts are obtained in situ in a known manner from the compounds of formula VIb, may be reacted with haloalcohols of the general formula XII,

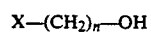
$X—(CH_2)_n—OH$ wherein n has the above meaning and X is halogen. To prepare compounds of formula X in which Z represents the group $NR^5$, compounds of formula VIb may be reacted with aminoalcohols of the general formula XIII,

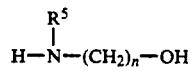
$$H—\underset{\underset{R^5}{|}}{N}—(CH_2)_n—OH$$

wherein $R^5$ and n have the above meanings. The reactions of the compounds of formula VIb to form the compounds of formula X may be carried out under the reaction conditions given above for the reaction of compounds of formula VI with compounds of formula VII.

Compounds of the general formula IIIb,

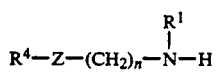
$$R^4—Z—(CH_2)_n—\underset{\underset{H}{|}}{\overset{\overset{R^1}{|}}{N}}—H$$

in which $R^1$, $R^4$, Z and n have the above meanings, may be obtained by reducing amides of the general formula XIV,

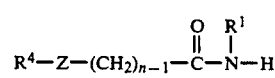
$$R^4—Z—(CH_2)_{n-1}—\overset{\overset{O}{\|}}{C}—\underset{\underset{H}{|}}{\overset{\overset{R^1}{|}}{N}}—H$$

wherein $R^1$, $R^4$, Z and n have the above meanings, in a known manner. The reduction may take place, for example, under the conditions given above for reducing compounds of formula IV.

Compounds of formula IIIb may also be obtained by reacting compounds of formula IIIa with an amine of the general formula IX, $$R^1-NH_2$$

wherein $R^1$ has the above meaning. The reaction may be carried out according to conventional methods for aminoalkylation, for instance under the conditions given above for the reaction of compounds of formula II with compounds of formula III. In order to avoid secondary reactions, it is advantageous to use a several-fold excess of the amine of formula IX.

Compounds of the general formula IIIc, $$R^4-Z'-(CH_2)_n-\underset{\underset{R^1}{|}}{N}-H$$

wherein $R^1$, $R^4$, $Z'$ and n have the above meanings, may also be obtained from compounds of the general formula XVII, $$R^4-Z'-(CH_2)_n-\underset{\underset{R^1}{|}}{N}-B$$

wherein $R^1$, $R^4$, $Z'$, n and B have the above meanings, by hydrogenolytic cleaving the group B. The cleaving may be carried out by catalytic hydrogenation, for instance under the conditions given above for preparing compounds of formula Ia according to method variant c). Compounds of formula XVII may themselves be prepared by reacting corresponding compounds of formula IIIa with amines of the general formula IX', $$R^1-N\begin{matrix}\diagup H\\ \diagdown B\end{matrix}$$

wherein $R^1$ and B have the above meanings.

Amides of formula XIV may be obtained by reacting acids of the general formula XV, $$R^4-Z-(CH_2)_{n-1}-CO-OH$$

wherein $R^4$, Z and n have the above meanings, or reactive acid derivatives thereof, with amines of formula IX in a known manner. Thus, reactive derivatives of the acids XV, particularly the acid halides thereof, preferably acid chlorides, esters and mixed anhydrides, e.g. mixed anhydrides with sulfonic acids, may be reacted with the amines of formula IX according to conventional methods to form amide groupings by aminoacylation. The aminoacylation may be carried out in a solvent which is inert under the reaction conditions at temperatures between room temperature and the boiling temperature of the solvent. Suitable solvents include halogenated hydrocarbons such as dichloromethane or chloroform, aromatic hydrocarbons such as benzene, toluene, xylene or chlorobenzene, cyclic ethers such as tetrahydrofuran or dioxane, or mixtures of these solvents. The aminoacylation may optionally be carried out in the presence of an acid-binding reagent, particularly if an acid halide or mixed acid anhydride is used. Organic bases, for instance tertiary lower alkylamines and pyridines, are particularly suitable as acid-binding agents. If acid halides are used, the reaction may also be carried out in a known manner in an aqueous medium and in the presence of inorganic bases according to the method of Schotten-Baumann. If the acid itself is used, the reaction is advantageously carried out in the presence of a coupling reagent known from peptide chemistry to be suitable. Particular examples of coupling reagents which promote amide formation with the free acid by reacting with the acid in situ, to form a reactive acid derivative, include alkyl carbodiimides, preferably cycloalkyl carbodiimides such as dicyclohexyl carbodiimide, or N-lower alkyl-2-halopyridinium salts, in particular halides or tosylates, preferably N-methyl-2-chloropyridinium iodide (see, Mukayama in Angew. Chemie 91, 789-912). The reaction in the presence of a coupling reagent may for instance be carried out at temperatures of $-30°$ to $+100°$ C., using solvents such as halogenated hydrocarbons and/or aromatic solvents in the presence of an acid-binding amine.

Acids of formula XV may be obtained by reacting compounds of the general formula VIa, $$R^4-Z-H$$

wherein $R^4$ and Z have the above meanings, with halocarboxylic acids of the general formula XVI, $$X-(CH_2)_{n-1}-CO-OH$$

wherein n and X have the above meanings. The reaction of compounds of formula VIa with the acids of formula XVI may be carried out in a known manner under conventional reaction conditions for formation of ethers or thioethers or for aminoalkylation. For instance, salts of the acids of formula XVI may be reacted under basic conditions with alkali metal salts of those compounds of formula VIa in which Z represents oxygen or sulfur, or with compounds of formula VIa, in which Z represents $NR^5$. The reaction may, for instance, be carried out under the conditions given for the reaction of compounds of formula VI with compounds of formula VII.

Acids of formula XV wherein n is 3 may also be obtained by reacting compounds of formula VIa with acrylic acid derivatives, preferably acrylonitrile, and then hydrolyzing the reaction product. The reaction product of the compounds of formula VIa with acrylonitrile may also be reduced directly to amines of formula IIIb in which n is 3 and $R^1$ is hydrogen.

Compounds of the general formula II are known or may be prepared according to known methods or analogously to known methods. For instance, compounds of formula II may be obtained starting from corresponding acids of the general formula VIII,

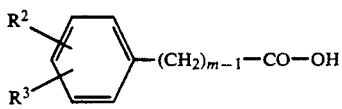

wherein $R^2$, $R^3$ and m have the above meanings. Thus reactive acid derivatives of the acids of formula VIII may be reacted with amines of formula IX to form corresponding amides, and these may then be reduced to form compounds of the general formula IIa,

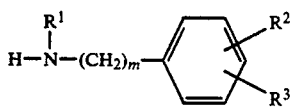

wherein $R^1$, $R^2$, $R^3$ and m have the above meanings. Acids of formula VIII may also be reduced to form the corresponding alcohols, and the hydroxy group may be converted in a known manner into a group Y to obtain compounds of the general formula IIb,

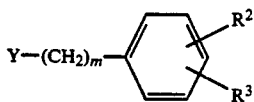

wherein $R^2$, $R^3$, m and Y have the above meanings. Acids of formula VIII are known or may be obtained in known manner. The amide compounds of the general formula IV may be obtained by reacting the acids of formula XV with amines of formula IIa according to conventional methods for amid formation under conventional conditions for aminoacylation.

Compounds of formula V may be obtained by reacting compounds of the general formula IIId,

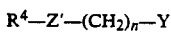
$$R^4-Z'-(CH_2)_n-Y$$

wherein $R^4$, $Z'$, n and Y have the above meanings, with compounds of the general formula XVIII,

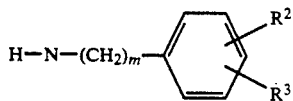

wherein $R^2$, $R^3$, m' and B have the above meanings. The reaction may take place in a known manner for aminoalkylation, for instance under the conditions given for the reaction of compounds of formula II with compounds of formula III.

Compounds of formula XVIII may be obtained by reacting corresponding acids of formula VIII in known manner with an amine of the general formula IX″, $$B-NH_2$$

wherein B has the above meaning, and reducing the resulting amide.

Compounds of formula XVIII may also be obtained starting from amines of the general formula IIc,

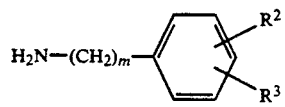

wherein $R^2$, $R^3$ and m' have the above meanings. For instance, amines of formula IIc may be reacted with an optionally substituted benzaldehyde, and the Schiff's base obtained as reaction product may then be reduced to form compounds of formula XVIII. Thus, the compounds of formula IIc may be reacted with the aldehyde under reducing conditions, for instance under the conditions given above for reductive alkylation of compounds of formula I for subsequently introducing an alkyl radical $R^1$.

Compounds of the general formula VId, $$R^4-OH$$

wherein $R^4$ has the above meaning, are known. The other compounds of formula VI may be prepared in a known manner from compounds of formula VId. To prepare the compounds of formula VIb, for instance, the hydroxy group of the compounds of formula VId may be converted into a group Y in a known manner. Compounds of formula VIe can be obtained starting with compounds of formula VId or compounds of formula VIb. For this purpose, the hydroxy group of the compounds of formula VId is first replaced by halogen, and the resulting halides of formula VIb are then reacted with potassium thioacetate to form compounds of the general formula XIX, $$R^4-S-CO-CH_3$$

wherein $R^4$ has the above meaning. The alkali metal salt of the compound of formula VIe is then obtained therefrom by treatment with an alkali metal alkoxide, and can be used directly for the further reactions.

Compounds of the general formula VIf,

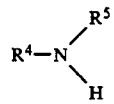

wherein $R^4$ and $R^5$ have the above meanings, may be obtained by reacting compounds of formula VIb with an excess of an amine of the general formula XX, $$R^5-NH_2$$

wherein $R^5$ has the above meaning, or by reacting the compound of formula VIb with an amine of the general formula XX',

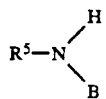

wherein $R^5$ and B have the above meanings, and then hydrogenolytically cleaving the group B. Compounds of formula VIf in which the $NR^5$ group is linked directly to a ring carbon atom, may also be produced by reacting a ketone corresponding to the respective alcohol VId with an amine of formula XX and reducing the resulting Schiff's base under conventional conditions for reductive alkylation.

Compounds of formula VII may be obtained in known manner by reacting a haloalcohol of formula XII with an amine of the general formula IId,

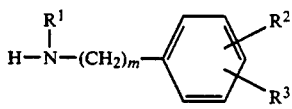

wherein $R^{1'}$, $R^2$, $R^3$, and m have the above meanings, to form compounds of the general formula VIIb,

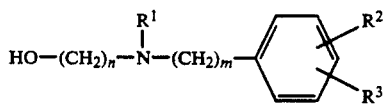

wherein R[1'], R[2], R[3], m and n have the above meanings. The other compounds of formula VII may be obtained from the compounds of formula VIIb by exchanging the hydroxy group for a different radical T' in a known manner. For instance, the hydroxy group of the compounds of formula VIIb may first be converted in known manner into a group Y, and the resulting compounds of formula VIIa may be reacted further in a known manner to form compounds of formula VII in which T' represents a group ZH in which Z is sulfur or NR[5].

The following examples are intended to illustrate the invention in greater detail, but without limiting its scope.

The Rf values, which are given in the following examples to characterize substances, were determined by thin layer chromatography on silica gel/glass plates (produced by Merck AG, type Si60F254). Unless otherwise stated, dichloromethane/diethyl ether (1:1) was used as the mobile phase.

The stereoisomeric forms of the compounds given in the examples may contain up to about 5% of other stereoisomeric forms of these compounds.

EXAMPLE 1

N-(2-[((1S,2S,5S)-6,6-dimethylbicyclo[3,1,1]hept-2-yl)methoxy]-ethyl)-N-(phenethyl)-N-methylamine A) 60 g (−)-cis-myrtanol (=((1S,2S,5S)-6,6-dimethylbicyclo[3,1,1]hept-2-yl)-methanol) were dissolved in 500 ml toluene. 9.9 g metallic sodium were added in portions to the solution with stirring and external cooling. Then the reaction mixture was stirred at a temperature of 80° C. until the sodium had completely dissolved. Then 89 g disodium iodide acetate were added, and the reaction mixture was refluxed for 40 hours. To work up the reaction mixture, after cooling it was diluted with dichloromethane and extracted twice with aqueous 2N sodium hydroxide solution. The aqueous phase was separated, rendered acidic with 6N hydrochloric acid solution, and extracted three times with dichloromethane. The combined dichloromethane extracts were dried over sodium sulfate, and the solvent was distilled off at reduced pressure. 13.4 g liquid cis-myrtanyloxy acetic acid were obtained as a residue and were processed further in the next stage without additional purification.

B) 7.7 g of the product obtained above were dissolved in 50 ml dichloromethane. 5 ml methanesulfonic acid chloride were added to the solution at a temperature of 0° C. Then 11 ml triethylamine and a small quantity of pyridine were added carefully in drops at a temperature of 0° C., and the reaction mixture was then stirred for two hours at 0° C. and for a further 2 hours at room temperature. 5 ml N-methyl-N-phenethylamine were added to the solution containing the mixed anhydride of the cis-myrtanyloxy acetic acid and methane sulfonic acid, and the reaction mixture was stirred for a further 5 hours at room temperature. To work up the reaction mixture it was extracted twice with 100 ml portions of aqueous 2N sodium hydroxide solution. The organic phase was dried over sodium sulfate and evaporated at reduced pressure. The oily crude product which remained as a residue was purified by chromatography on silica gel at slightly elevated pressure (flash chromatography) using ether/dichloromethane as eluent. 6.8 g oily N-(methyl)-N-(phenethyl)-[((1S,2S,5S)-6,6-dimethyl-bicyclo[3,1,1]hept-2-yl)-methoxy]-acetamide were obtained. Rf value=0.4.

C) 1.2 g lithium aluminium hydride were suspended in 20 ml of a mixture of tetrahydrofuran/toluene (7:3) with nitrogen gassing. A solution of 6.8 g of the oily product obtained above under B) in 30 ml of tetrahydrofuran/toluene mixture was added in drops to the suspension at boiling temperature, and the reaction mixture was refluxed for 5 hours. To work up the reaction mixture, 1.2 ml water, 1.2 ml 15% aqueous sodium hydroxide solution and another 3.5 ml water were added consecutively and carefully to the reaction mixture after cooling, in order to decompose excess lithium aluminium hydride. After the reaction had ended, the reaction mixture was filtered, and the filtrate was concentrated by evaporation at reduced pressure. The remaining residue was dissolved in ether and extracted twice with 50 ml portions of 2N aqueous hydrochloric acid. The hydrochloric aqueous phase was separated, rendered alkaline and extracted with ether. The ether extract was dried over sodium sulfate and concentrated at reduced pressure. The remaining oily crude title compound was purified by chromatography on silica gel using ether/dichloromethane (1:1 as eluent. 2.5 g of N-(2-[((1S,2S,5S)-6,6-dimethylbicyclo[3,1,1]hept-2-yl)-methoxy]-ethyl)-N-(phenethyl)-N-methylamine were obtained. Rf value=0.15.

For conversion into its hydrochloride, the compound was dissolved in ether; gaseous hydrogen chloride was added to the solution, and the solution was then evaporated. The amorphous hydrochloride of N-(2-[((1S,2S,5S)-6,6-dimethylbicyclo[3,1,1]hept-2-yl)-methoxy]-ethyl)-N-(phenethyl)-N-methylamine was obtained having a melting point of 160° C. $[\alpha]_D^{20} = -5.1°$ (c=1; in methanol).

EXAMPLE 2

N-(3-[((1S.2S,5S)-6,6-dimethylbicyclo[3,1,1]hept-2-yl)methoxy]-propyl)-N-(phenethyl)-N-methylamine A) 51 g cis-myrtanol were dissolved in a little dichloromethane. 5.5 g benzyl-trimethyl ammonium hydroxide (=Triton B) were added to the solution. Then 32.5 ml acrylonitrile were added in drops to the reaction mixture with ice cooling, whereby the internal temperature was regulated to between 30° and 40° C. Once the reaction had ended, the reaction mixture was diluted with 200 ml dichloromethane and washed twice with 100 ml portions of aqueous dilute hydrochloric acid solution. Then the organic phase was concentrated by evaporation. 71 g crude 3-(1S,2S,5S)-6,6-dimethylbicyclo[3,1,1]hept-2-yl)-methoxy]propionic acid nitrile were obtained as a liquid oil. Rf value=0.6.

B) 60 g of the oily product obtained above were stirred in 200 ml concentrated aqueous hydrochloric acid solution for 8 hours at room temperature. Then the reaction mixture was extracted with dichloromethane. The dichloromethane extract was evaporated, and the remaining residue was purified by chromatography on silica gel using dichloromethane/ether (1:1) as eluent. 28 g of 3-[((1S,2S,5S)-6,6-dimethylbicyclo[3,1,1]hept-2-yl)-methoxy]propionic acid were obtained. Rf value=0.15.

C) 8.1 g of the acid obtained above were dissolved in dichloromethane as described in Example 1B) and converted by reacting with 5 ml methanesulfonic acid chloride into the mixed anhydride, which was reacted further with 10 ml N-methyl-N-phenethylamine, 11.1 ml triethylamine and a small quantity of pyridine in dichloromethane, as described in Example 1B). The resulting crude product was purified by chromatography on silica gel using dichloromethane/ether (1:1) as eluent. 9 g N-methyl-N-(phenethyl)-3-[((1S,2S,5S)-6,6-dimethylbicyclo[3,1,1]hept-2-yl)-methoxy]-propionamide were obtained. Rf value=0.5.

D) 8 g of the amide obtained above were reduced with 1.4 g lithium aluminium hydride in 50 ml of a mixture of tetrahydrofuran/toluene (7:3) as described in Example 1C). The reaction mixture was worked up as described in Example 1C). 3 g N-(3-[((1S,2S,5S)-6,6-dimethylbicyclo[3,1,1]hept-2-yl)-methoxy]-propyl)-N-(phenethyl)-N-methylamine were obtained. Rf value=0.15.

EXAMPLE 3

N-(4-[2-((1S,2S,5S)-6,6-dimethylbicyclo[3,1,1]hept-2yl)-ethoxy]-butyl)-N-(phenethyl)-N-methylamine A) 200 g cis-dihydronopol (=2-((1S,2S,5S)-6,6dimethylbicyclo[3,1,1]hept-2-yl)-ethanol) were dissolved in 340 ml toluene. 200 ml thionyl chloride were added in drops to the solution. Then 5 ml dimethyl formamide were added, and the reaction mixture was stirred for 4 hours under reflux. To work up the reaction mixture the solvent was distilled off at reduced pressure, the residue was taken up in 300 ml toluene, again concentrated to dryness, and again taken up in 300 ml toluene and concentrated to dryness. 206 g crude 2((1S,2S,5S)-6,6-dimethylbicyclo[3,1,1]hept-2-yl)ethyl chloride were obtained which were processed further in the next stage without additional purification.

B) 12.2 g elemental sodium were dissolved in portions spread over 12 hours in 320 ml 1,4-butanediol at a temperature of 90° C. Then 80 g 2-((1S,2S,5S)-6,6dimethylbicyclo[3,1,1]hept-2-yl)-ethyl chloride were added in drops to this solution, and the reaction mixture was heated to 130° C. for 15 hours. In order to work up the reaction mixture it was cooled to room temperature, then 300 ml of a 5% aqueous hydrochloric acid solution were added, and the mixture was extracted with ether. After evaporation of the ether extract, 95.2 g crude 4-[2-((1S,2S,5S)-6,6dimethylbicyclo[3,1,1]hept-2-yl)-ethoxy]-butanol were obtained.

C) 90 g of the product obtained above were dissolved in 110 ml toluene. 1 ml dimethyl formamide was added to the solution, and then 62 ml thionyl chloride were added in drops at room temperature, and the reaction mixture was stirred for 3 hours under reflux. The reaction mixture was worked up as described in Example 3A). 95.1 g crude 4-[2-((1S,2S,5S)-6,6-dimethylbicyclo[3,1,1]hept-2-yl)-ethoxy]butyl chloride were obtained which were immediately processed further in the next reaction stage. Rf value=0.7.

D) 5 g of the product obtained above were stirred under reflux with 3.2 ml N-methyl-N-phenethylamine and 2.9 ml triethylamine for 5 hours at a bath temperature of 130° C. After cooling, 100 ml dichloromethane were added to the reaction mixture, and the resulting solution was washed with 50 ml 2N aqueous sodium hydroxide solution and with 50 ml water, dried over sodium sulfate and concentrated by evaporation. The crude title compound remaining as a residue was purified by chromatography on silica gel using dichloromethane/ether (1:1) as eluent. 4.4 g N-(4-[2-((1S,2S,5S)-6,6-dimethylbicyclo[3,1,1]hept-2-yl)ethoxy]butyl)-N-(phenethyl)-N-methylamine were obtained. Rf value=0.15.

For conversion into its hydrochloride, the substance was dissolved in ether, gaseous hydrogen chloride was added to the solution, and the solution was then evaporated. 4.4 g amorphous hydrochloride of N-(4-[2-((1S,2S,5S)-6,6dimethylbicyclo[3,1,1]hept-2-yl)-ethoxy]-butyl)-N-(phenethyl)-N-methylamine with a melting point of 60° C. were obtained. $[\alpha]_D^{20} = -11.5°$ (c=1; methanol).

EXAMPLE 4

N-(4-[2-((1S,2S,5S)-6,6-dimethylbicyclo[3,1,1]hept-2yl)-ethoxy]-butyl)-N-[2-(3,4-dimethoxyphenyl)-ethyl]-N-methylamine 7 g 4-[2-((1S,2S,5S)-6,6-dimethylbicyclo[3,1,1]hept-2-yl)-ethoxy]-butyl chloride, 5.8 g N-methyl-homoveratrylamine, 4 ml triethylamine and a catalytic quantity of potassium iodide were refluxed in 10 ml acetonitrile for 8 hours. Then the reaction was stopped and 150 ml dichloromethane were added to the reaction mixture after it had become cold. The resulting solution was washed with 70 ml aqueous 2N sodium hydroxide solution and then twice with water, dried over sodium sulfate, and the solvent was distilled off. The crude title compound which remained as a residue was purified by chromatography on silica gel using ethyl acetate/methanol (8:2) as eluent. 4.8 g N-(4-[2-((1S,2S,5S)-6,6-dimethylbicyclo[3,1,1]hept-2-yl)-ethoxy]butyl)-N-[2-(3,4-dimethoxyphenyl)ethyl]-N-methylamine were obtained. Rf value=0.2. In addition, it was possible to isolate 2.3 g of unreacted 4-[2-((1S,2S,5S)-6,6-dimethylbicyclo[3,1,1]hept-2-yl)ethoxy]-butyl chloride. Rf value=0.6.

The title base was converted into its hydrochloride as described in Example 3D. 4.8 g N-(4-[2-((1S,2S,5S)-6,6-dimethylbicyclo[3,1,1]hept-2-yl)-ethoxy]-butyl)-N-[2-(3,4-dimethoxyphenyl)-ethyl]-N-methylamine hydrochloride were obtained. $[\alpha]_D^{20} = -9.5°$ (c=1; methanol).

EXAMPLE 5

N-(3-[2-((1S,2S,5S)-6,6-dimethylbicyclo[3,1,1]hept-2yl)-ethoxy]-propyl)-N-(phenethyl)-N-methylamine A) 15 g 3-[2-((1S,2S,5S)-6,6-dimethylbicyclo[3,1,1-]hept-2-yl)-ethoxy]-propanol (prepared analogously to Example 3B) from 2-((1S,2S,5S)-6,6-dimethylbicyclo[3,1,1]hept-2-yl)-ethyl chloride and 1,3-propanediol) were dissolved in 50 ml dichloromethane. 9.2 ml methanesulfonic acid chloride, 20.4 ml triethylamine and a small quantity of pyridine were added successively to the solution at a temperature of 0° C. The reaction mixture was stirred for 2 hours at room temperature. Then the solvent was distilled off at reduced pressure. The 3-[2-((1S,2S,5S)-6,6-dimethylbicyclo[3,1,1]hept-2-yl)-ethoxy]-propyl mesylate remaining as residue was immediately processed further in the following reaction stage.

B) The product obtained above was dissolved in 20 ml N-methyl-N-phenethylamine. A catalytic quantity of copper I iodide and some sodium carbonate were added to the solution, and the reaction mixture was stirred for 6 hours at a bath temperature of 100° C. After cooling the mixture was worked up by diluting with 150 ml dichloromethane, washing the organic phase with saturated aqueous hydrogen carbonate solution and then with water, drying over sodium sulfate, and concentrating by evaporation. The remaining crude product was freed from impurities by chromatography on silica gel using dichloromethane/ether (1:1) and then eluted from the silica gel acid with the addition of methanol. 7.8 g N-(3-[2-((1S,2S,5S)-6,6-dimethylbicyclo[3.1.1]hept-2-yl)-ethoxy]-propyl)-N-(phenethyl)-N-methylamine were obtained. Rf value=0.1 (solvent dichloromethane/ether 1:1).

C) 25.5 g of the title base obtained above were dissolved in 30 ml tetrahydrofuran. 4.3 ml orthophosphoric acid were added to the solution. The reaction mixture was allowed to stand for 30 minutes at room temperature. Then the solvent was evaporated at reduced pressure, and the resulting residue was recrystallized from 30 ml isopropanol. The resulting crude hydrogen phosphate of the title compound was again stirred in 100 ml ether at reflux temperature, then the solvent suction filtered using a glass frit, and the remaining crystals were dried in an oil pump vacuum. 29.2 g crystalline N-(3-[2-((1S,2S,5S)-6,6-dimethylbicyclo[3,1,1]hept-2-yl)-ethoxy]-propyl)-N-(phenethyl)-N-methylammonium dihydrogen phosphate were obtained having a melting point of 103° C. $[\alpha]_D^{20}= -10.4$ (c=1; methanol).

EXAMPLE 6

N-(3-[2-((1S,2S,5S)-6,6-dimethylbicyclo[3,1,1]hept-2yl)-ethylthio]-propyl)-N-(phenethyl)-N-methylamine A) 15.6 g triphenylphosphine were dissolved in 300 ml acetonitrile, and 3.02 ml bromine were added to the solution in drops with vigorous stirring at a temperature of 0° C. Then a solution of 10 g cisdihydronopol (=2-((1S,2S,5S)6,6-dimethylbicyclo[3,1,1]hept-2-yl)-ethanol) in 100 ml acetonitrile was added, and the reaction mixture was heated to 100° C. (bath temperature) for 5 hours. The reaction mixture was worked up by distilling off the solvent under reduced pressure, and the residue was purified chromatographically over silica gel using dichloromethane as eluent. 12.0 g 2-((1S,2S,5S)-6,6dimethylbicyclo[3,1,1]hept-2-yl)-ethyl bromide were obtained.

B) 4 g of the product obtained above were dissolved in 20 ml dimethyl formamide. 2.0 g potassium thioacetate were added to the solution, and the reaction mixture was stirred for 14 hours at room temperature. Then the precipitated potassium bromide was filtered out, and the solvent was distilled off at reduced pressure. The remaining residue was purified chromatographically over silica gel using toluene/cyclohexane as eluent. 3.8 g 2-((1S,2S,5S)-6,6-dimethylbicyclo[3,1,1]hept-2-yl)-ethyl thioacetate were obtained. Rf value=0.4 (solvent toluene/cyclohexane).

C) 3.8 g of the product obtained above were dissolved in a little absolute methanol. 1.05 g sodium methylate were to the solution under exclusion of moisture, and the solution was stirred for 3 hours at room temperature. Then 1.6 ml 3-bromopropanol were added to the solution containing the sodium salt of 2-((1S,2S,5S)-6 6-dimethylbicyclo[3,1,1]hept-2-yl)-thioethanol, and the reaction mixture was refluxed for 8 hours. During this time, two 0.2 ml portions of 3-bromopropanol were added. In order to work up the reaction mixture, it was poured onto aqueous 6N hydrochloric acid and the mixture was extracted twice with 100 ml portions of dichloromethane. The organic extracts were dried over sodium sulfate and concentrated by evaporation. The remaining residue was purified chromatographically over silica gel using ethyl acetate/n-hexane (1:4) as eluent. 1.8 g3-[2-((1S,2S,5S)-6,6-dimethylbicyclo[3,1,1-]hept-2-yl)ethylthio]-propanol were obtained. Rf value=0.4.

D) 1.8 g of the product obtained above-were dissolved in 30 ml dichloromethane. 0.65 ml methanesulfonic acid chloride were added to the solution at a temperature of 0° C., and then 1.5 ml triethylamine were carefully added. The reaction mixture was stirred for 2 hours at room temperature. To work up the reaction mixture, the solvent was distilled off at reduced pressure. The residue containing the resulting 3-[2-((1S,2S,5S)-6,6dimethylbicyclo[3,1,1]hept-2-yl)-ethylthio]-propyl)-methane sulfonate was dissolved in 30 ml acetonitrile. 0.9 g N,N-dimethylaminopyridine and 1.2 ml N-methyl-N-phenethylamine were added to the solution, and the reaction mixture was refluxed for 16 hours. To work up the reaction mixture, the acetonitrile was distilled off at reduced pressure, and the remaining residue was purified chromatographically over silica gel using dichloromethane/methanol (9:1) as eluent. 1.1 g N-(3-[2-((1S,2S,5S)-6,6-dimethylbicyclo[3,1,1]hept-2-yl)-ethylthio]-propyl)-N-(phenethyl)-N-methylamine were obtained. Rf value=0.5 (mobile solvent methanol/ethyl acetate 3:7). $[\alpha]_D^{20}= -17.0$ (c=1; methanol).

EXAMPLE 7

N,N'-dimethyl-N-[2-((1S,2S,5S)-6 6-dimethylbicyclo[3,1,1]hept-2-yl)-ethyl]-N'-(phenethyl)-1,2-diaminoethane A) 3.4 ml N-methylaminoethanol and 7.3 ml triethylamine were added to 12.4 g 2-((1S,2S,5S)-6,6-dimethylbicyclo[3,1,1]hept-2-yl)-ethyl bromide, and the reaction mixture was stirred for 6 hours at room temperature. To work up the reaction mixture it was chromatographed over silica gel using dichloromethane/methanol (8:2) as solvent. 3.8 g N-methyl-N-[2-((1S,2S,5S)-6,6-dimethylbicyclo[3,1,1]hept-2-yl)-ethyl]-2-aminoethanol were obtained. Rf value=0.4. Furthermore, 7 g unreacted starting material were recovered.

B) 3.8 g of the product obtained above were dissolved in 50 ml dichloromethane. 1.7 ml methanesulfonic acid chloride and then 3.8 ml triethylamine were added carefully to the solution at a temperature of 0° C. The reaction mixture was stirred for 2 hours at room temperature. Then the solvent was distilled off at reduced pressure. The residue containing the resulting N-methyl-N-[2-((1S,2S,5S)-6,6-dimethylbicyclo[3,1,1]hept-2-yl)-ethyl]-2-aminoethyl methane sulfonate was dissolved in 50 ml acetonitrile. 2.5 ml triethylamine and 2.8 ml N-methyl-N-phenethylamine were added to the solution, and the reaction mixture was refluxed for 8 hours. To work up the reaction mixture it was poured onto 150 ml saturated aqueous sodium bicarbonate solution, and the resulting mixture was extracted three times with 50 ml portions of dichloromethane. The combined dichloromethane extracts were washed with 50 ml water and dried over sodium sulfate. Then the solvent was evaporated, and the crude title compound which remained as a residue was purified by chromatography on silica gel using dichloromethane/methanol (9:1) as eluent. 2 g N,N'-dimethyl-N-[2((1S,2S,5S)-6,6-dimethylbicyclo[3,1,1]hept-2-yl)-ethyl]-N'-(phenethyl)-1,2-diaminoethane were obtained. Rf value=0.5 (mobile solvent: dichloromethane/methanol, 9:1).

For conversion into its hydrochloride, this base was dissolved in ether, gaseous hydrogen chloride was added to the solution, and the solution was evaporated. 1.7 g amorphous dihydrochloride of the title compound were obtained. $[\alpha]_D^{20} = -13.2°$ (c=1; methanol).

EXAMPLE 8

N-(4-[2-((1S,2S,5S)-6,6-dimethylbicyclo[3,1,1]hept-2yl)-ethoxy]-butyl)-N-[2-(3,4-dimethoxyphenyl)-ethyl]amine A) 8.4 g benzaldehyde and 9 g homoveratrylamine were dissolved in 100 ml ethanol. Raney nickel was added to the solution, and the mixture was hydrogenated for 2 hours at room temperature and a hydrogen pressure of 5 bar. Then the catalyst was filtered out, the filtrate was evaporated at reduced pressure, and the residue was taken up in 100 ml dichloromethane. The dichloromethane phase was washed with water, dried over sodium sulfate and concentrated by evaporation. After the oily residue had been triturated with ether, 10.9 g solid N-benzylhomoveratrylamine were obtained, which was processed further without additional purification.

B) 10.9 g of the product obtained above and 8.5 g 4-[2-((1S,2S,5S)-6,6-dimethylbicyclo[3,1,1]hept-2-yl)ethoxy]butyl chloride were dissolved in 100 ml acetonitrile. After the addition of potassium carbonate, the reaction mixture was refluxed for 4 hours. The reaction mixture was subsequently filtered, the filtrate was concentrated by evaporation, and the remaining residue was purified by chromatography on silica gel using dichloromethane/ether as eluent. 8 g oily N-(4-[2-((1S,2S,5S)-6,6-dimethylbicyclo[3,1,1]hept-2-yl)-ethoxy]-butyl)-N-[2-(3,4-dimethoxyphenyl)ethyl]-N-benzylamine were obtained.

C) 3 g of the product obtained above were dissolved in a mixture of 100 ml ethanol and 30 ml water. 1.5 g concentrated hydrochloric acid solution and 2.5 g hydrogenation catalyst (5% palladium/carbon) were added consecutively to the solution, and the mixture was hydrogenated at room temperature and a hydrogen pressure of 4 bar. The absorption of hydrogen finished after approximately 3 hours. The catalyst was filtered out of the mixture, and the filtrate was concentrated by evaporation at reduced pressure. The remaining residue was taken up in 100 ml water and extracted with ethyl acetate. The organic phase was dried over sodium sulfate, filtered and concentrated at reduced pressure. The resulting crude title compound was purified by chromatography over silica gel using ethyl acetate/methanol (7:3) as eluent. 1.8 g oily N-(4-[2-((1S,2S,5S)-6,6-dimethylbicyclo[3,1,1]hept-2-yl)ethoxy]-butyl)-N-[2-(3,4-dimethoxyphenyl)-ethyl]-amine were obtained. Rf value=0.1 (mobile solvent: ethyl acetate/methanol, 9:1).

For conversion into its hydrochloride, the title base was dissolved in ether, gaseous hydrogen chloride was added to the solution, and the solution was then evaporated. The amorphous hydrochloride of N-(4-[2-((1S,2S,5S)-6,6-dimethylbicyclo[3,1,1]hept-2-yl)-ethoxy]-butyl)-N-[2-(3,4-dimethoxyphenyl)-ethyl]-amine was obtained having a melting range of 115-120° C. $[\alpha]_D^{20} = -10.8°$ (c=1; in methanol).

EXAMPLE 9

N-[2-((1S,3S,4R)-1-methyl-4-isopropylcyclohex-3-yloxy)ethyl]-N-phenethylamine

A) 2.8 g D-menthyloxyacetic acid (=((1S,3S,4R)-1-methyl-4-isopropylcyclohex-3-yloxy)-acetic acid) were dissolved in 50 ml dichloromethane. 1.8 ml methanesulfonic acid chloride, 4 ml triethylamine and a small quantity of pyridine were added consecutively to the solution at a temperature of 0° C. The reaction mixture was stirred for 2 hours at room temperature. Then the solvent was distilled off at reduced pressure. The mixed anhydride of D-menthyloxyacetic acid and methanesulfonic acid which remained as a residue was immediately processed further in the following reaction stage.

B) The product obtained above was dissolved in 5 ml phenethylamine, and the reaction mixture was stirred for 4 hours at room temperature. To work up the reaction mixture, it was dissolved in 100 ml dichloromethane, the solution was washed twice with 50 ml portions of 1N aqueous hydrochloric acid solution and once with 50 ml water, and dried over sodium sulfate. Then the solvent was distilled off. 4 g N-(phenethyl)-((1S,3S,4R)-1-methyl-4-isopropylcyclohex-3-yloxy)-acetamide remained as a residue. Rf value=0.6 (mobile solvent: ethyl acetate/methanol, 7:3).

C) 4 g of the amide obtained above were reduced in 60 ml tetrahydrofuran/toluene mixture with 0.7 g lithium aluminium hydride according to the method described in Example 1C. The reaction mixture was then worked up as described in Example 1C. The crude title compound which remained as a residue was purified by chromatography on silica gel using ethyl acetate/methanol (7:1). 1.9 g oily N-[2-((1S,3S,4R)-1-methyl-4-isopropylcyclohex-3-yloxy)ethyl]-N-phenethylamine were obtained. Rf value=0.3 (mobile solvent: ethyl acetate/methanol).

The title base was converted into its hydrochloride as described in Example 1C. 1.7 g N-[2-((1S,3S,4R)-1-methyl-4-isopropylcyclohex-3-yloxy)-ethyl]-N-phenethylamine hydrochloride were obtained having a melting range of 120-145° C. $[\alpha]_D^{20} = +59.5°$ (c=1; in methanol).

EXAMPLE 10

N-(4-[2-((1S,2S,5S)-6,6-dimethylbicyclo[3,1,1]hept-2yl)-ethoxy]-butyl)-N-[2

3gN-(4-[2-((1S,2S,5S)-6,6-dimethylbicyclo[3,1,1]hept-2-yl)-ethoxy]-butyl)-N-[2-(3,4-dimethoxyphenyl)-ethyl]amine (for preparation, see Example 8), 1 g methyl iodide and 0.5 g potassium carbonate were stirred in 10 ml acetonitrile for 2 hours at room temperature. Then the reaction mixture was heated to 50° C. for another 4 hours. To work up the reaction mixture it was cooled, diluted with 150 ml dichloromethane, washed twice with water, dried over sodium sulfate, and filtered. The solvent was distilled off, and the remaining residue was purified by chromatography on silica gel using ethyl acetate/methanol (8:2) as eluent. 2.1 g N-(4-[2-((1S,2S,5S)-6,6-dimethylbicyclo[3,1,1]hept-2-yl)-ethoxy]butyl)-N-[2-(3,4-dimethoxyphenyl)-ethyl]-N-methylamine were obtained. Rf value=0.1 (solvent: dichloromethane/ether, 1:1).

2.1 g of the title base were converted into the corresponding hydrochloride as described in Example 4. 2.2 g N-(4-[2-((1S,2S,5S)-6,6-dimethylbicyclo[3,1,1]hept-2-yl)ethoxy]-butyl)-N-[2-(3,4-dimethoxyphenyl)-ethyl]-

N-methylamine hydrochloride were obtained. $[\alpha]_D^{20} = -9.5°$ (c=1; methanol).

The compounds of formula I listed in the following Table I were also obtained by methods analogous to the foregoing examples.

TABLE I

| Example No. | $R^1$ | n | m | Z | $R^2$ | $R^3$ | $R^4$ | Salt Form | melting point (melting range) in °C. | $[\alpha]_D^{20}$ in °(c = 1 CH$_3$OH) |
|---|---|---|---|---|---|---|---|---|---|---|
| 11 | CH$_3$ | 2 | 2 | O | H | H | trans-myr. | HCl | 150 | −15.1 |
| 12 | CH$_3$ | 2 | 2 | O | H | H | L-menth. | HCl | 80–100 | −53.5 |
| 13 | H | 2 | 2 | O | H | H | L-menth. | HCl | 100–120 | −57.4 |
| 14 | (CH$_3$)$_2$—CH | 2 | 2 | O | H | H | L-menth. | HCl | oil | −46.5 |
| 15 | CH$_3$ | 2 | 2 | O | 3,4-di-CH$_3$O— | | L-menth. | HCl | 110–130 | −42.5 |
| 16 | (CH$_3$)$_2$—CH | 2 | 2 | O | 3,4-di-CH$_3$O— | | L-menth. | HCl | oil | −40.2 |
| 17 | CH$_3$ | 3 | 2 | O | H | H | L-menth. | HCl | 138–140 | −52.3 |
| 18 | H | 5 | 3 | O | H | H | cis-dihydronop. | HCl | 120–140 | −12.0 |
| 19 | H | 5 | 4 | O | H | H | cis-dihydronop. | HCl | 130–140 | −10.9 |
| 20 | CH$_3$ | 3 | 2 | O | H | H | cis-dihydronop. | Ba | oil | −13.4 |
| 21 | CH$_3$ | 5 | 2 | O | H | H | cis-dihydronop. | HCl | oil | −12.5 |
| 22 | CH$_3$ | 5 | 2 | O | 3,4-di-CH$_3$O— | | cis-dihydronop. | HCl | oil | −9.2 |
| 23 | H | 5 | 2 | O | 3,4-di-CH$_3$O— | | cis-dihydronop. | HCl | 130–140 | −11.2 |
| 24 | H | 4 | 2 | O | 2-CH$_3$O— | H | cis-dihydronop. | HCl | 130–135 | −11.5 |
| 25 | H | 5 | 2 | O | 2-CH$_3$O— | H | cis-dihydronop. | HCl | oil | −11.2 |
| 26 | CH$_3$ | 2 | 2 | S | H | H | cis-dihydronop. | Ba | oil | −17 |
| 27 | H | 5 | 2 | O | 2-Cl— | H | cis-dihydronop. | HCl | 110–120 | −11.3 |
| 28 | CH$_3$ | 3 | 2 | O | 3,4-di-CH$_3$O— | | cis-dihydronop. | HCl | 70–80 | −10.2 |
| 29 | H | 4 | 1 | O | 3,4-di-Cl— | | cis-dihydronop. | HCl | 170–178 | −10.7 |
| 30 | H | 5 | 1 | O | 3-CF$_3$— | H | cis-dihydronop. | HCl | 86–90 | −10.3 |
| 31 | H | 4 | 1 | O | 3-CH$_3$— | H | cis-dihydronop. | HCl | 130–140 | −12.7 |
| 32 | H | 4 | 1 | O | 3-F— | H | cis-dihydronop. | HCl | 130–135 | −11.2 |
| 33 | H | 4 | 1 | O | 3,4-O—CH$_2$—O— | | cis-dihydronop. | HCl | 178–180 | −11.2 | cis-dihydronop. = cis-dihydronopyl = 2-((1S,2S,5S)-6,6-dimethylbicyclo[3,1,1]hept-2-yl)ethyl;
HCl = hydrochloride
cis-myr. = cis-myrtanyl = (1S,2S,5S)-6,6-dimethylbicyclo[3,1,1]hept-2-yl)-methyl;
Ba = base
trans-myr. = trans-myrtanyl = (1S,2R,5S)-6,6-dimethylbicyclo[3,1,1]hept-2-yl)-methyl;
oil = oily
L-menth. = L-menthyl = (1R,3R,4S)-1-methyl-4-isopropyl-cyclohex-3-yl

EXAMPLE I

Tablets were produced having the following composition per tablet:

| | |
|---|---|
| N-(3-[2-((1S,2S,5S)-6,6-dimethylbicyclo[3,1,1]hept-2-yl)-ethoxy]-propyl)-N-(phenethyl)-N-methylammonium dihydrogen phosphate | 20 mg |
| Corn starch | 60 mg |
| Lactose | 135 mg |
| Gelatine (as 10% solution) | 6 mg |

The active substance, the corn starch and the lactose were thickened with the 10% gelatine solution. The paste was comminuted, and the resulting granules were placed on a suitable tray and dried at 45° C. The dried granules were passed through a grinding machine and mixed in a mixer with the following further auxiliaries:

| | |
|---|---|
| Talcum | 5 mg |
| Magnesium stearate | 5 mg |
| Corn starch | 9 mg | and then pressed into 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I:

$$R^4-Z-(CH_2)_n-\underset{\underset{R^1}{|}}{N}-(CH_2)_m-\underset{R^3}{\overset{R^2}{\text{Ar}}}$$

wherein
m represents 1–4,
n represents 2–5,
$R^1$ is hydrogen or lower alkyl,
$R^2$ is hydrogen, lower alkyl, lower alkoxy, halogen or trifluoromethyl, and
$R^3$ is hydrogen, lower alkyl, lower alkoxy or halogen, or
$R^2$ and $R^3$ are linked to adjacent carbon atoms and together form an alkylenedioxy group with 1–2 carbon atoms,
$R^4$ represents a saturated monocyclic or bicyclic terpene hydrocarbon radical with 10 carbon atoms, or a bicyclic hydrocarbon radical with 11 carbon atoms corresponding to the formula a:

$$\text{bicyclic structure with two CH}_3\text{ groups}-CH_2-CH_2-$$

and
Z represents oxygen, an N—$R^5$ group in which $R^5$ is lower alkyl, or if $R^4$ is a group of formula a, Z also may be sulfur, and physiologically acceptable acid addition salts thereof.

2. A compound according to claim 1, wherein $R^4$ represents a monocyclic or bicyclic hydrocarbon group with 10 or 11 carbon atoms selected from the group consisting of: 2-(6,6-dimethylbicyclo[3,1,1]hept-2-yl)-ethyl (=dihydronopyl) of formula a,

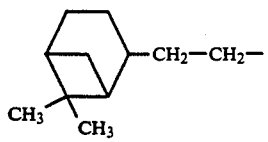

1-methyl-4-isopropylcyclohex-3-yl (=menthyl) of formula b,

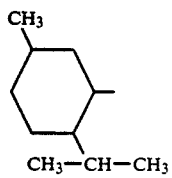

6,6-dimethylbicyclo[3,1,1]hept-2-ylmethyl (=myrtanyl) of formula c,

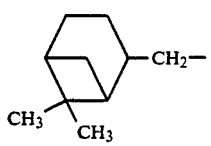

lieu 1,3,3-Trimethylbicyclo[2,2,1[hept-2-yl (=fenchyl) of formula d,

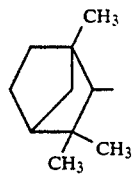

and 1,7,7-trimethylbicyclo[2,2,1]hept-2-yl (=bornyl) of formula e,

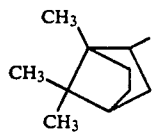

3. A compound according to claim 2, wherein $R^4$ represents a group corresponding to one of the formulas a, b and c.

4. A compound according to claim 3, wherein $R^4$ represents a 2-(6,6-dimethylbicyclo[3,3,1]hept2-yl)-ethyl group.

5. A compound according to claim 4, wherein the $R^4$ group is predominantly present in the 1S,2S,5S-configuration.

6. A pharmaceutical composition comprising a compound according to claim 1, in an amount effective to exhibit a pharmacological activity selected from the group consisting of gastrointestinal mucosa protecting activity, gastrointestinal ulcer-inhibiting activity, and gastrointestinal spasmolytic activity, and at least one conventional pharmaceutical carrier or adjuvant.

7. A method of inhibiting ulceration of the gastrointestinal mucosa of a mammal comprising administering to said mammal an effective ulcer-inhibiting amount of a compound corresponding to the formula I:

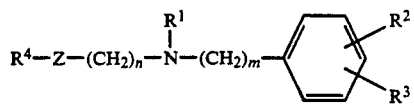

wherein
m represents 1-4,
n represents 2-5,
$R^1$ is hydrogen or lower alkyl,
$R^2$ is hydrogen, lower alkyl, lower alkoxy, halogen or trifluoromethyl, and
$R^3$ is hydrogen, lower alkyl, lower alkoxy or halogen, or
$R^2$ and $R^3$ are linked to adjacent carbon atoms and together form an alkylenedioxy group with 1-2 carbon atoms,
$R^4$ represents a saturated monocyclic or bicyclic terpene hydrocarbon radical with 10 carbon atoms, or a bicyclic hydrocarbon radical with 11 carbon atoms corresponding to the formula a:

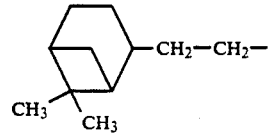

and
Z represents oxygen, an N—$R^5$ group in which $R^5$ is lower alkyl, or if $R^4$ is a group of formula a, Z also may be sulfur,
or a physiologically acceptable acid addition salt thereof.

8. A method according to claim 7, wherein $R^4$ represents a monocyclic or bicyclic hydrocarbon group with 10 or 11 carbon atoms selected from the group consisting of: 2-(6,6-dimethylbicyclo[3,1,1]hept-2-yl)-ethyl (=dihydronopyl) of formula a,

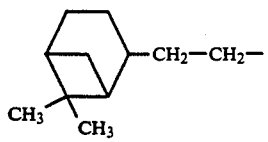

1-methyl-4-isopropylcyclohex-3-yl (=menthyl) of formula b,

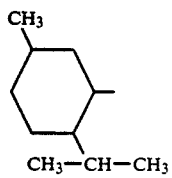

6,6-dimethylbicyclo[3,1,1]hept-2-ylmethyl (=myrtanyl) of formula c,

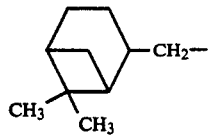

1,3,3-trimethylbicyclo[2,2,1]hept-2-yl (=fenchyl) of formula d,

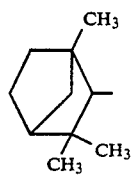

and 1,7,7-trimethylbicyclo[2,2,1]hept-2-yl (=bornyl) of formula e,

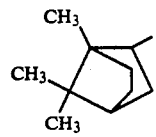

9. A method according to claim 8, wherein $R^4$ represents a group corresponding to one of the formulas a, b and c.

10. A method according to claim 9, wherein $R^4$ represents a 2-(6,6-dimethylbicyclo[3,1,1]hept-2-yl)-ethyl group.

11. A method according to claim 10, wherein the $R^4$ group is predominantly present in the 1S,2S,5S-configuration.

12. A method according to claim 7, wherein said compound is administered as a unit dose containing from 10 to 200 mg of said compound.

13. A method according to claim 7, wherein said compound is administered in admixture with a pharmaceutically acceptable carrier or diluent.

14. A method according to claim 13, wherein said carrier or diluent is selected from the group consisting of lactose, starch, talcum and liquid paraffins.

15. A method according to claim 13, wherein said compound is administered in admixture with at least one adjuvant selected from the group consisting of tablet disintegrating agents, solubilizers and preservatives.

16. A method according to claim 7, wherein said compound is administered in a pharmaceutical dosage form selected from the group consisting of tablets, capsules, suppositories and solutions.

* * * * *